United States Patent [19]

Hladky

[11] Patent Number: 4,575,678
[45] Date of Patent: Mar. 11, 1986

[54] CORROSION MONITORING

[75] Inventor: Karel Hladky, Manchester, England

[73] Assignee: The University of Manchester Institute of Science and Technology, Manchester, England

[21] Appl. No.: 455,709

[22] Filed: Jan. 5, 1983

[30] Foreign Application Priority Data

Jan. 5, 1982 [GB] United Kingdom ............... 8200196

[51] Int. Cl.⁴ ............................................. G01N 27/00
[52] U.S. Cl. .................................... 324/425; 204/404; 324/71.2; 324/348
[58] Field of Search ............... 324/71.1, 71.2, 65 CR, 324/425, 348, 349, 447, 72; 204/1 C, 404

[56] References Cited

U.S. PATENT DOCUMENTS

| 2,374,088 | 4/1945 | Fontana et al. | 204/404 |
| 2,777,111 | 1/1957 | Hunter | 324/348 |
| 3,365,376 | 1/1968 | Weyland | 324/447 |
| 4,322,805 | 3/1982 | Rog et al. | 324/72 |

FOREIGN PATENT DOCUMENTS 743948 1/1944 Fed. Rep. of Germany ........ 324/65 CR

OTHER PUBLICATIONS

Iverson, Warren P., "Transient Voltage Changes Produced in Corroding Metals and Alloys", J. of Electrochemical Soc.: Electrochemical Science, Jun. 1968.

Primary Examiner—Ernest F. Karlsen
Assistant Examiner—Kevin D. O'Shea
Attorney, Agent, or Firm—Sughrue, Mion, Zinn, Macpeak, and Seas

[57] ABSTRACT

In an apparatus or installation having a metal part corroding in an electrolyte contacting the part, that part is a first electrode electrically insulated from a second electrode, for example another part of the apparatus, also contacting the electrolyte. No external electrical power is applied to the electrodes/electrolyte system. The low frequency voltage between the electrodes is observed. This voltage is a low frequency noise signal. Amplitude values of the signal are measured and subjected to an averaging computation yielding data indicating the corrosion rate of the first electrode and the nature of the corrosion.

9 Claims, 18 Drawing Figures

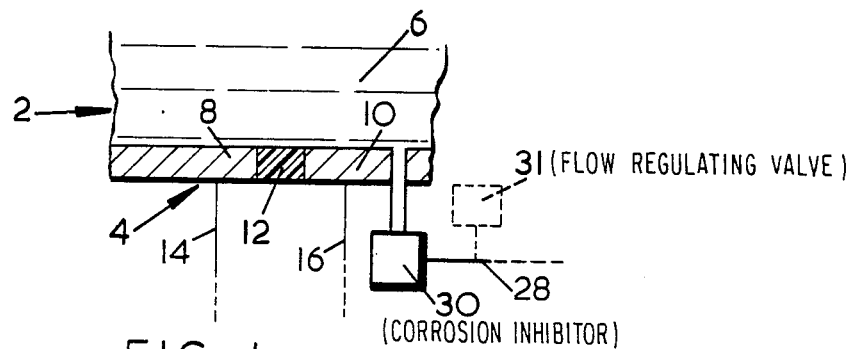
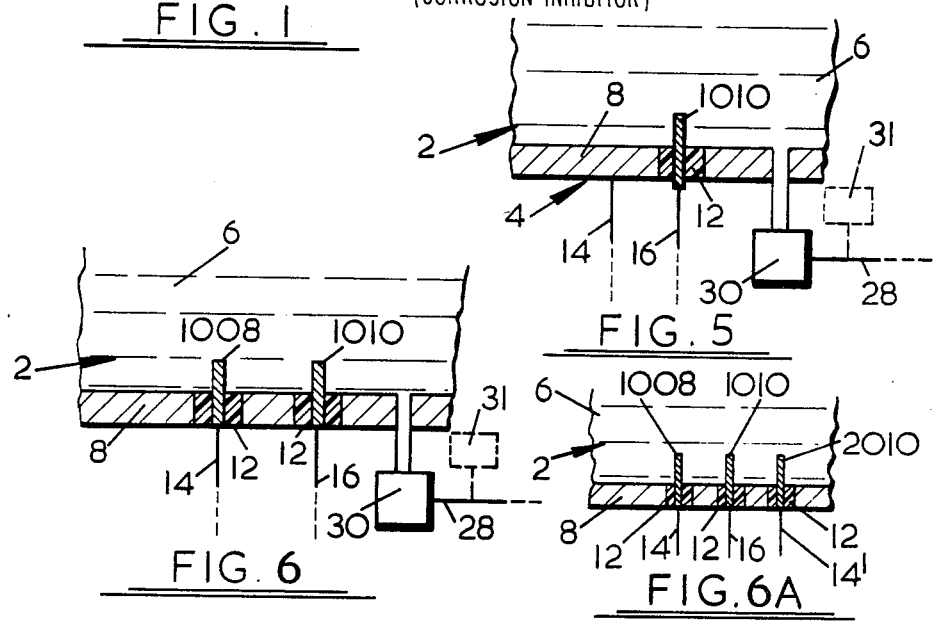

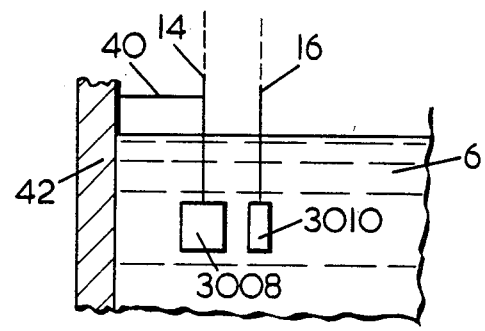
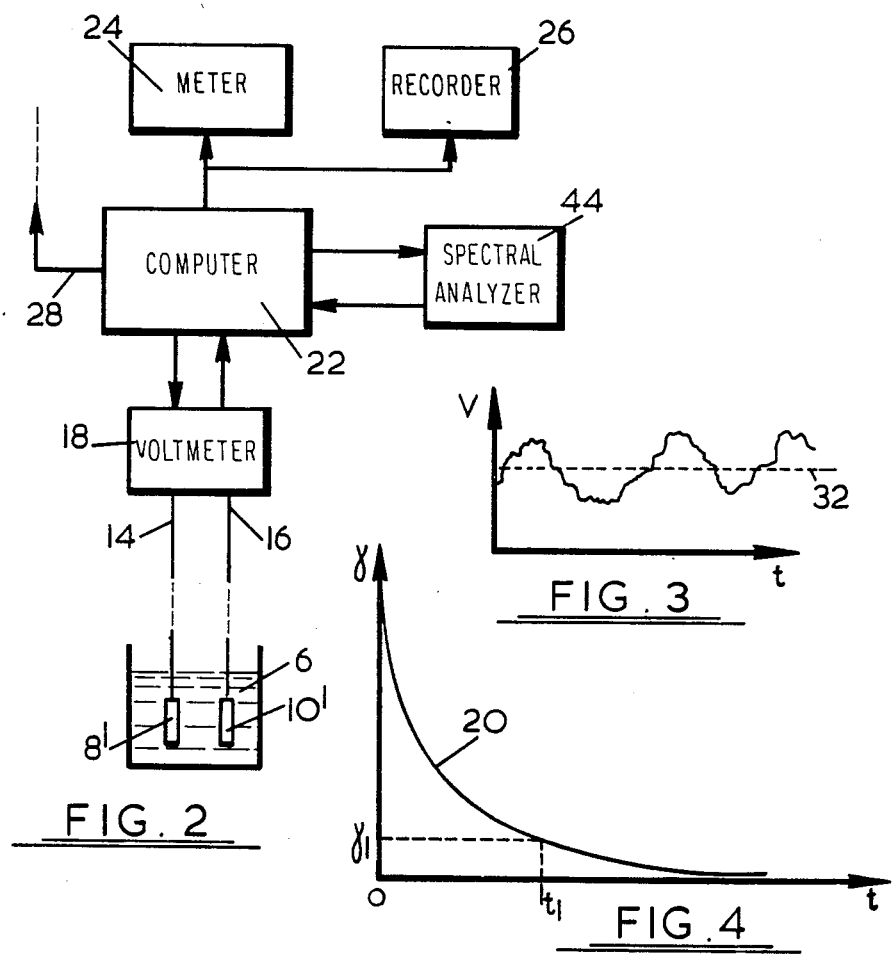

CORROSION MONITORING

This invention concerns monitoring corrosion of a metal part of an apparatus or installation.

According to the invention there is provided a method of monitoring corrosion of a metal part of an apparatus or installation in which the part constituting a first electrode is in contact with an electrolyte and is corroding, comprising connecting a voltmeter between the first electrode and a second electrode in contact with said electrolyte but otherwise electrically insulated from the first electrode, said second electrode being non- or substantially non-corrodable in said electrolyte or said second electrode corroding in the electrolyte at a rate which does not exceed the rate of corrosion of the first electrode, said electrodes and electrolyte forming a system to which no current or voltage is applied from any source external to the system, using the voltmeter to make a measurement of the voltage between the electrodes, and using the voltage measurement to provide indication of at least one characteristic of corrosion of the first electrode.

The voltage measured at any instant is, or is a function of, the corrosion potential of the first electrode in the electrolyte and is the result of naturally occurring reactions, for example metal dissolution and hydrogen evolution and/or errosion of the electrode under the effects of cavitation in the electrolyte such as in high velocity fluid systems.

The potential difference between the two electrodes is a voltage noise signal which fluctuates at rather low frequency. For example, in the noise signal the highest component frequency worth observing appears not to exceed 10 Hz and an appropriate range can have about 1 Hz as the upper frequency limit, though for practical purposes observation of the range of component frequencies between about 1 mHz and about 100 mHz appears satisfactory. The voltages observed are low and require measurement to the order of milli or microvolts for example, and accordingly the voltmeter must be very sensitive.

The invention will now be further described, by way of example, with reference to the accompanying drawings in which:

FIG. 1 diagrammatically shows, partly in section, a fragment of an apparatus or installation to which the method according to the invention can be applied;

FIG. 2 shows diagrammatically equipment which can be used to perform the method according to the invention;

FIG. 3 is a diagrammatic representation of the kind of curve which may be obtained by plotting against time t the fluctuating voltage of the noise signal i.e. the voltage between the first and second electrodes;

FIG. 4 is a diagrammatic representation of a curve showing a variation of corrosion rate $\gamma$ with respect to time t;

Figure 13:
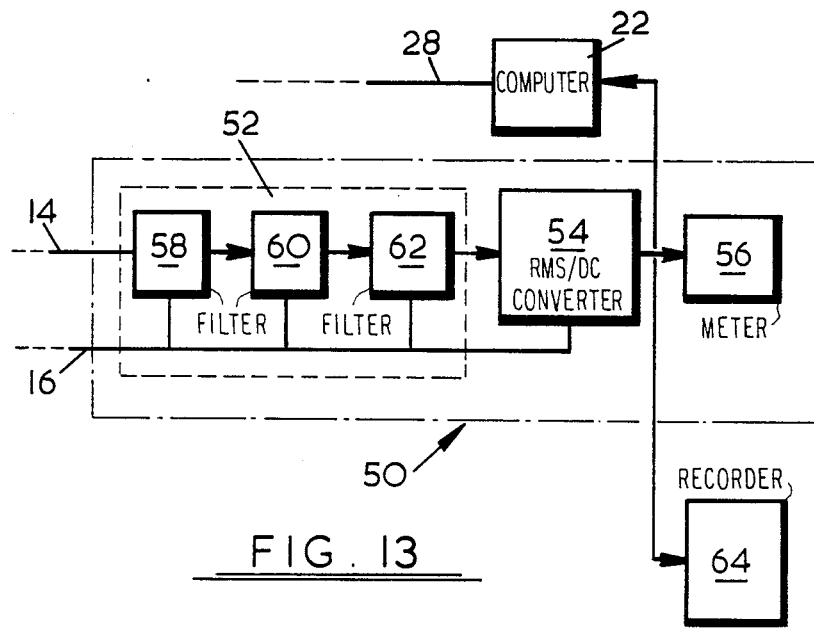
Figure 9:
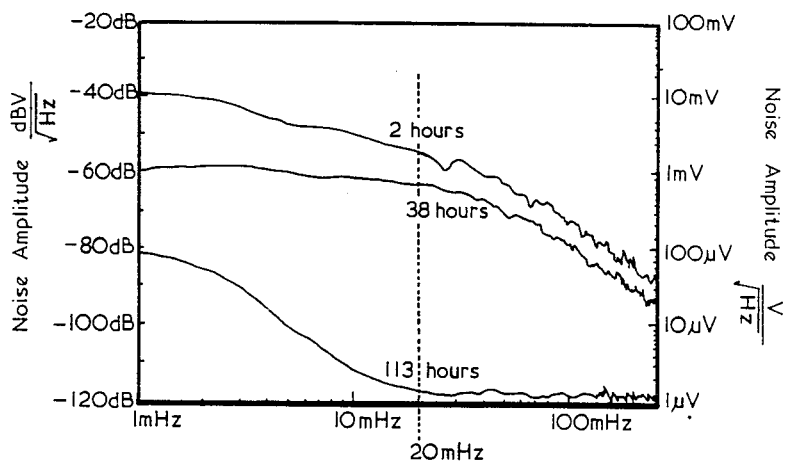
Figure 10:
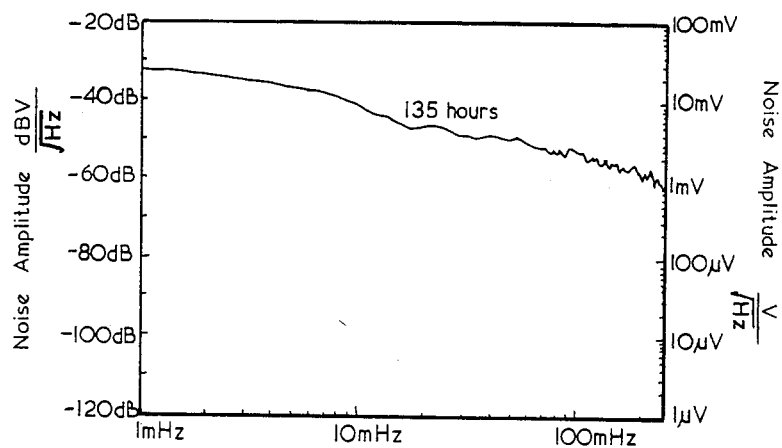
Figure 11:
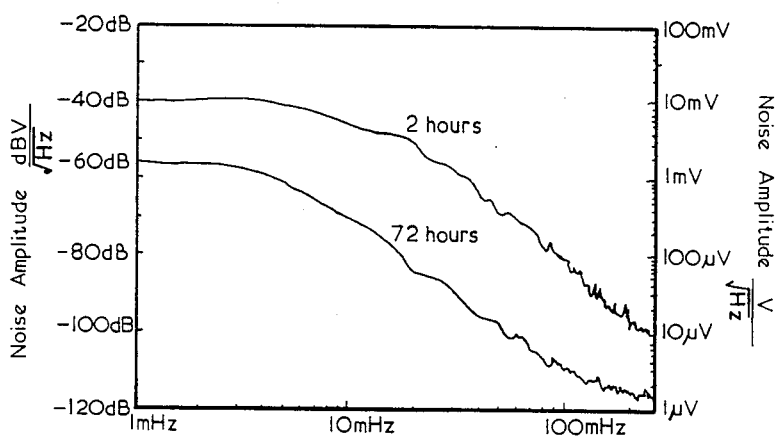
Figure 12:
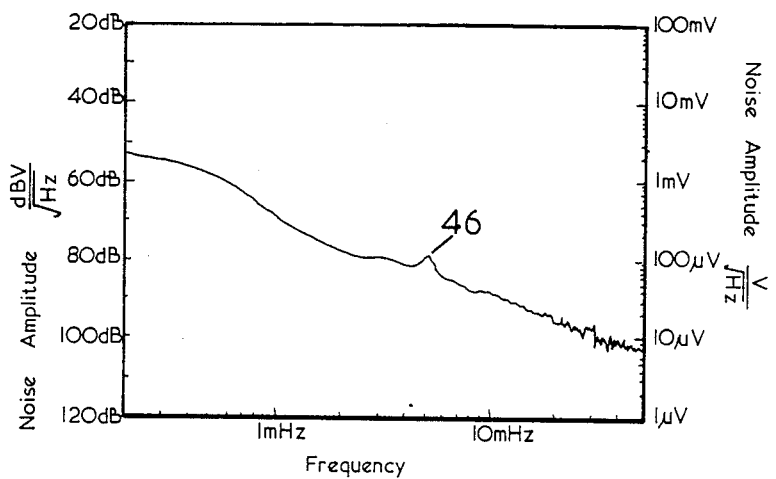
Figure 14:
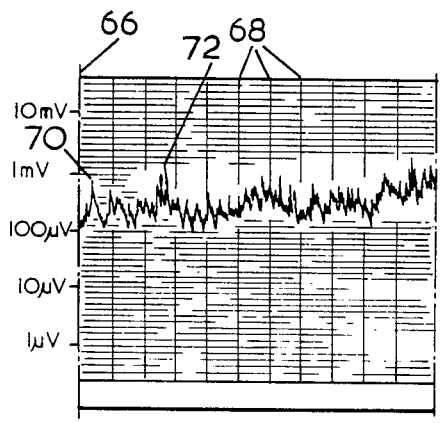
Figure 15A:
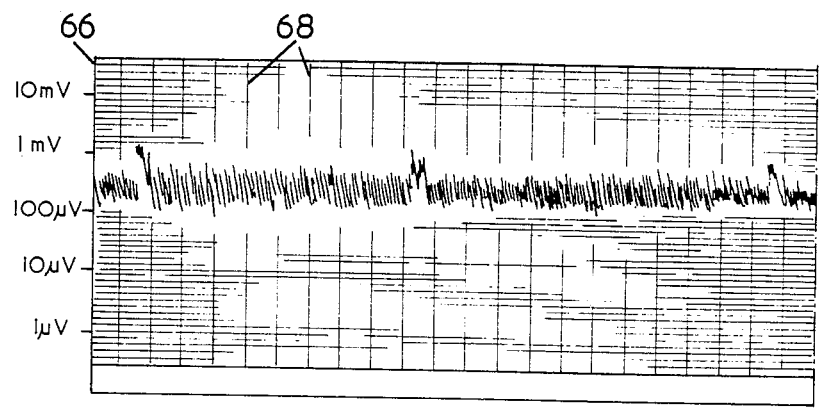
Figure 15B:
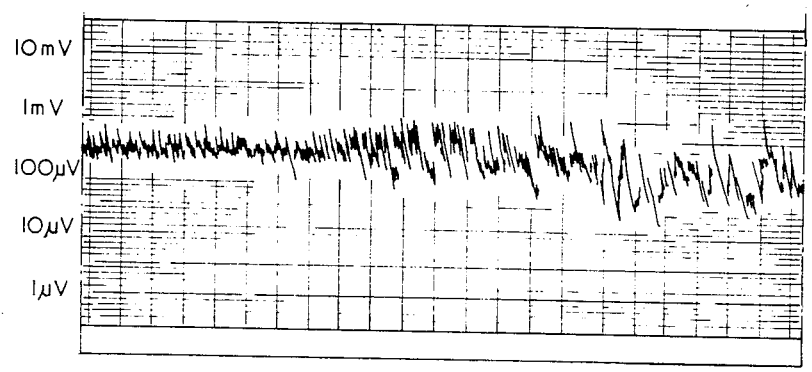
Figure 15C:
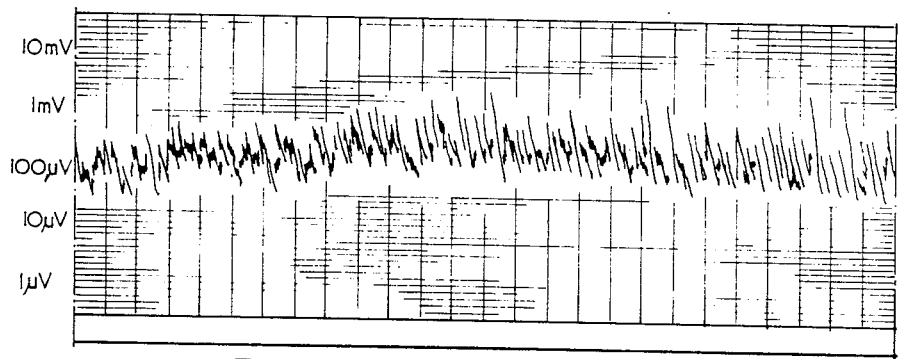

FIGS. 5 and 6 diagrammatically show modifications of the apparatus or installation in FIG. 1, and FIG. 6A shows a modification of the arrangement in FIG. 6;

FIG. 7 diagrammatically shows, partly in section, a fragment of a concrete installation in which the method according to the invention is being performed using as the first electrode metal reinforcement within a mass of concrete;

FIG. 8 is a diagrammatic illustration of an apparatus or installation in which corrosion of a sacrificial electrode is being monitored according to the invention;

FIG. 9 shows a plurality of graphs representing electrochemical noise amplitude spectra obtained using copper electrodes in aerated sea water;

FIG. 10 shows a graph representing an electrochemical noise amplitude spectrum obtained using aluminium electrodes in aerated sea water;

FIG. 11 shows graphs representing electrochemical noise amplitude spectra obtained using mild steel electrodes in aerated sea water;

FIG. 12 shows a graph representing an electrochemical noise amplitude spectrum obtained using electrodes of "memory" alloy (Ti-Ni) in dilute hydrochloric acid, e.g. 0.3M HCl;

FIG. 13 shows diagrammatically alternative equipment which can be used to perform the method according to the invention;

FIGS. 14 and 15 each diagrammatically show a fragment of a chart record, made over a time period of a variable which is a function of amplitude of the voltage of a predetermined band of frequencies forming part of an electrochemical noise voltage signal providing the potential difference between a pair of mild steel electrodes in aerated water containing 1000 ppm of sodium chloride, the record in FIG. 14 being of a corrosion attack comprising pitting, the record in FIG. 15 being of a corrosion attack comprising crevice attack, and FIG. 15 consisting of FIGS. 15A, 15B and 15C in which FIG. 15B follows in time immediately after FIG. 15A and FIG. 15C follows in time immediately after FIG. 15B.

In FIG. 1 an apparatus or installation is indicated generally at 2. This installation 2 has a metal portion 4 which is being corroded by dissolution into electrolyte 6 and/or by erosion under the effect of cavitation in the electrolyte. The term "apparatus or installation" 2 can include any sort of equipment, construction, plant or portion thereof (static or mobile) coming into contact with electrolyte and can include a variety of liquid containing means for example, a pipe or conduit, a storage tank, process vessel, heat exchanger, a pump, or a valve unit.

In FIG. 1 the portion 4 is divided into two parts 8 and 10 electrically insulated from one another by insulation 12. Part 8 forms a first electrode connected to an electric lead 14, and part 10 of the same material as part 8 forms a second electrode connected to lead 16. Leads 14 and 16 in FIG. 1 are connected to a voltmeter 18 shown in FIG. 2. FIG. 3 shows a type of cyclically varying noise signal (formed by low frequency components) the voltmeter would observe over a time t of at least several minutes duration.

If a sample piece of known weight of metal of substantially identical kind as the part 8 is disposed in electrolyte of substantially the same kind as electrolyte 6 under substantially the same conditions as prevail between part 8 and electrolyte 6, the sample can be weighed after elapse of successive periods of time and its weight loss due to corrosion obtained after elapse of each time period. From this the corrosion rate $\gamma$ of the sample in units of weight per unit time can be calculated at each time of observation. FIG. 4 shows a curve 20 illustrating variation of corrosion rate $\gamma$ with time t.

Returning to FIGS. 1 and 2 at any instant the voltage measured by voltmeter 18 is the amplitude at that instant of the low frequency electrical noise signal which is the resultant of a mixture of a plurality of signals of different discrete frequencies. The voltage measurement may be sampled at predetermined intervals under control of a computer 22 over a predetermined time duration which may be equal to or exceed the period of the lowest discrete frequency of which it is desired to take account. The standard deviation D of the samples (i.e. the voltage amplitude of the noise) taken over said duration is then calculated after the drift in the corrosion potential (i.e. the macro trend) has been removed by normal computing techniques.

The rate of corrosion $\gamma$ is proportional to the standard deviation D, and is a linear function of the product of $C \times D$ where C is a constant i.e. $\gamma = C \times D$. The value of C for the particular metal of part 8 in particular electrolyte 6 under the particular conditions in the apparatus 2 can be determined in the laboratory by a technique to be described below. Therefore since C is known the rate of corrosion $\gamma$ of electrode 8 can be calculated. If the standard deviation D is calculated at a time $t_1$ in FIG. 4 then from curve 20 the rate of corrosion is $\gamma 1$, by integrating to determine the area under curve 20 between time limit 0 and $t_1$, the total weight loss of electrode 8 can be calculated. If its weight at the beginning observation and its thickness are known, then its total weight loss up to time $t_1$ is known. Also the time the remaining sound metal will take to corrode totally or to a predetermined extent can also be calculated using the information represented by FIG. 4. The data represented by FIG. 4 does not have to be pictorially represented but can be stored in computer 22 for comparison with input information and for access.

If desired a plurality of standard deviations $D_1, D_2, D_3$ etc, can be calculated in succession for successive time durations. These successive durations may overlap in which case a sample used in the calculation of the standard deviation relevant to one time duration may also be used in calculation of the standard deviation of a succeeding time duration. But a predetermined number of samples taken during an initial part of one time duration are omitted from the standard deviation calculation relevant to the next time duration and are replaced by samples taken over the final part of the next time duration.

For example, if the lowest discrete frequency it is wished to observe in the noise is 1 mHz this has a period of 1000 seconds. Therefore the time duration has to be at least 1000 seconds Thus taking as an example a time duration of 1000 seconds, samples may be taken at predetermined intervals of 1 second, i.e. a thousand per time duration. A standard deviation $D_1$ is calculated for the samples taken in the duration 0 to 1000 seconds, then, neglecting the samples taken over the time 0 to 100 seconds, the next standard deviation $D_2$ may be calculated using the samples taken in the duration commencing at 100 seconds and ending at 1100 seconds, and the following standard deviation $D_3$ may be calculated using samples taken in the duration starting at 200 seconds and ending at 1200 seconds and so on.

Preferably the voltmeter 18 is a digital voltmeter providing output readings in a binary code to computer means 20 controlling sampling and wherein the said standard deviations and/or the rates of corrosion are computed. The resultant numerical values may be displayed on meter 24 and/or printed as numbers and/or on a plotted curve using recorder 26. Also the computer 22 may give an output to meter 24 and/or recorder 26 to indicate the extent of corrosion and/or how long it will take to corrode the remaining sound metal or a predetermined amount of the remaining sound metal.

Except for very small electrodes, it appears that the voltage is independent of the surface area of the electrodes exposed to the electrolyte, and that the voltage measured corresponds to the maximum rate of corrosion occurring at any instant at any part of the surface of the first electrode in a general area thereof closest to the second electrode. Thus localised high corrosion is detected.

If a corrosion rate $\gamma$ is observed, for the part 8 of installation 2, in excess of a predetermined value computer 22 can, by path 28, signal operation of corrosion inhibition means 30 in FIG. 1 whereby, in the case of chemical corrosion one or more chemical corrosion inhibitors are released into electrolyte 6. In the case of cavitation corrosion gas bubbles which can be relatively large may be released into electrolyte 6, and/or flow conditions, for example the flow rate, of the electrolyte can be varied, for example automatically, in response to a signal on path 28, for example to cause operation of flow rate regulating value means (shown diagrammatically at 31 in FIGS. 1, 5 and 6) to reduce or stop the cavitation corrosion.

To determine the value of constant C in the laboratory two sample electrodes 8' and 10' shown in FIG. 2 in the electrolyte 6 are connected to the voltmeter 18 and the process carried out to derive standard deviation $D_1, D_2, D_3$ as described above. Since variation of corrosion rate $\gamma$ with time as exemplified by FIG. 4 is already known a standard deviation $D_1$ calculated in correspondence with time $t_1$ gives the value of constant $C = D_1/\gamma 1$. The value of C can be checked using standard deviation $D_2$ corresponding to a time $t_2$ on the abscissa from which the corrosion rate is $\gamma_2$ and so on.

Electrolyte 6 may be of very low conductivity, for example an organic fluid or a mixed phase system in which at least one of the fluids is an organic liquid.

Instead using the relationship $$\gamma = C \times D$$

other relationships for example $$\gamma = C1 \times R$$

or $$\gamma = C2 \times A$$

may be used in which C1 and C2 are constants, R is a root mean square value and A is an average value. Then instead of calculating standard deviations $D_1$, $D_2, D_3$ etc., for samples of the noise amplitude at timed intervals the corresponding root mean squares R1, R2, R3 etc. are computed after digital removal by the computer of the d.c. component in voltmeter output, or average noise amplitude values A1, A2, A3 corresponding to the timed intervals are computed after the computer has digitally rectified the voltmeter output falling below a reference datum level 32 in FIG. 3.

The second electrode in the installation 2 is preferably of the same material as the first electrode 8 as is the case in FIG. 1, since both electrodes of corrodable material causes a larger voltage to be observed than if the second electrode is of material which is inert with respect to the electrolyte 6. Nevertheless reference electrodes of such inert metal may be used.

In the apparatus or installation 2 in FIG. 5 the second electrode 1010 insulated by the insulation 12 from the electrode 8 can be a coupon of the same material as the part 8 or may be a reference probe electrode of material, for example, platinum or paladium, which is inert with respect to the electrolyte 6.

In FIG. 6 the first electrode 1008 in insulation 12 is a coupon of the same material as portion 8 and 10 so the corrosion rate of electrode 1008 is the same as those portions. The second electrode 1010 can also be a coupon or may be an inert reference probe.

If it is found that a reference probe 1010 is not wholly inert but corrodes in electrolyte 6, then as shown in FIG. 6A in more insulation 12 another reference probe electrode 2010 of the same material of probe 1010 can be provided. Switching means is provided whereby either lead 14 or 14' can be connected to the voltmeter 18 as desired. Then the computer uses the appropriate averaging process applied to the noise amplitude signal to calculate average A, root-mean square R or standard deviation Dx, for example, the standard deviation Dx, of the electrochemical noise of the two probes 1008, 1010. This value Dx is then subtracted from standard deviation Dy of the voltage noise across the coupon 1008 and reference probe 1010 to give a corrosion rate for the coupon of $C\sqrt{(Dy^2 - Dx^2)}$.

An installation 2 comprising reinforced concrete is shown in FIG. 7. Concrete mass 34 contains metal reinforcement 2008. In this instance a bore is drilled through the concrete 34 to the metal reinforcement 2008 or first electrode to which lead 14 from the voltmeter 18 (FIG. 2) is attached. The second electrode 2010, which may be a probe, on the outside of the concrete, is in contact with a store or supply of electrolyte, for example water, in a porous or absorbent carrier 36, for example a sponge, applied to an outer surface of the concrete. As shown, there can be a plurality of second electrodes 2010 contacting absorbent material spaced apart along the concrete along the length of the reinforcement therein. By closure of a particular switch means 38 a desired second electrode 2010 can be connected via line 16 to the voltmeter. The voltage reading between the reinforcement and any particular second electrode is a function of the rate of corrosion occurring at substantially that part of the reinforcement opposite the second electrode and using the method described above, the rate of corrosion can be obtained.

The monitoring method can be used in the installation 2 in FIG. 8 to observe the corrosion rate or efficiency of operation of a sacrificial electrode 3008, for example a sacrificial anode which may be of magnesium, aluminium or zinc material, to determine if the sacrificial electrode electrically connected via path 40 to metal part 42 is adequately protecting the metal 42 which normally corrodes quickly in the electrolyte 6. In this case the sacrificial anode 3008 forms the first electrode connected to the voltmeter 18 (FIG. 2) by line 14, and the second electrode 3010 is connected to the voltmeter by line 16. The electrode 3010 is located close to sacrificial electrode 3008 and is preferably inert to the electrolyte.

The corrosion potential of the first electrode measured by the voltmeter 18 (FIG. 2) may also be used to carry out spectral analysis of the noise signal to determine the noise amplitude voltage and phase or a function thereof (said amplitude voltage and phase or function being hereafter referred to as the ordinate value) of different discrete frequencies forming the noise signal.

From this spectral data it is possible to determine the nature of the corrosion, for example pitting or crevice corrosion, and possibly the extent of corrosion and the length of time over which corrosion has been taking place in a particular first electrode and electrolyte system.

A test sample of material similar to that of the first electrode is immersed in the electrolyte, which may be under similar conditions to the first electrode. The fluctuating corrosion potential noise signal as measured by the voltmeter between the test sample and a suitable second electrode is spectrally analysed and various ordinate values obtained corresponding to at least some respective discrete frequencies forming the noise signal. The spectrum data obtained is stored and if desired may be used to plot a curve of ordinate values against frequency. The nature of the sample corresponding to that data is observed, i.e. to see what sort of corrosion is taking place and its extent. At various intervals of time after the sample first contacts the electrolyte, further spectral analysis may be performed so a number of sets of spectra data can be obtained each set corresponding to a particular duration of corrosion.

Thus when spectral analysis of the corrosion potential signal is carried out using the first electrode instead of merely the sample the spectrum data obtained can be compared with the stored or recorded data relating to the sample and where correspondence is found it is then possible to tell what sort of corrosion is affecting the first electrode and possibly for how long corrosion has been occurring and thus to what extent the first electrode has become corroded.

Investigations lead one to believe that different types of corrosion give rise to different respective characteristic spectra. Accordingly, it would be possible to make a spectral analysis of the noise potential corresponding to any first electrode to determine whether or not the amplitude or phase spectral data reveal any particular characteristic. If such data is revealed then one could say what the nature of the corrosion of that first electrode is.

Amplitude and phase spectral analysis of the corrosion noise potential signal for different electrode materials may be performed, for example, in the following manner using the hereafter described apparatus which is shown in FIG. 2.

EXAMPLES OF SPECTRAL ANALYSIS

Description of apparatus

The apparatus of FIG. 2 used for the measurements employed a Hewlett-Packard HP-85A desk-top computer 22 acting as a controller for the IEEE-488 interface bus connecting all the other instruments. Potentials were measured with a Solatron 7055 digital microprocessor voltmeter 18 and amplitude spectra were computed after the output of the voltmeter was treated by the spectral analyser 44, for example a Hewlett-Packard HP3582A. Hardcopy plots of the results were then produced on a Hewlett-Packard 72225A graphics plotter 26.

Electrode noise was measured as the potential difference between two "identical" electrodes 8', 10'. This was found preferable to the more conventional reference electrode arrangement although both these techniques gave essentially identical results. The voltmeter used employed digital techniques for mains interference rejection and drift correction making it possible to measure electrode potentials to an accuracy of ±0.1 μV even in the presence of strong mains frequency fields without the need for any special screening arrangements.

The potential difference between the two electrodes was sampled by the voltmeter under programme control at a rate derived from the computer's internal clock. The readings were transferred to the computer and the resulting "time record" was digitally filtered using suitable mathematical manipulations of the data in order to remove the d.c. component and components at frequencies outside the range of interest. The time record, comprising 1024 data points was then transferred to the memory.

Eight consecutive amplitude spectra were root mean square (r.m.s.) averaged by the analyzer 44 and the result was transferred back to the computer. Spectral amplitude smoothing was then applied, again using suitable computational algorithms, and the resulting corrected amplitude spectrum was plotted on the graphics plotter and stored on magnetic tape cartridge.

The overall accuracy of measurement was limited by the resolution of the voltmeter. Dynamic range limitations resulted from the 16 bit arithmetic used to compute the transform restricting that range to ca 90 dB. In this respect there was a balancing of accuracy against speed.

The results presented below were obtained using an effective sampling rate of 1.024 Hz after filtering. Theoretically it was possible to measure over a frequency range of 1 mHz–0.512 Hz; practical limitations reduced this to 1–255 mHz with 1 mHz resolution. The results were corrected for the bandwidth of measurement and plotted as logarithm of frequency vs logarithm of amplitude $dBV/\sqrt{Hz}$.

Materials

The metals tested were 99.99% copper, an aluminium alloy containing 2.1% Mg and mild steel. Electrodes were made from these three metals, masked off with epoxy putty compounds and ground to a "1200" grit size finish. The exposed areas were 5 cm² for copper, 12.5 cm² for aluminium and 5.5 cm² for mild steel. Sea water was prepared from BDH Chemicals sea water mixture and the solution was aerated both before and during the test runs.

The eletrodes were set up in a cell vessel containing 500 ml of the test solution and were connected to the voltmeter with suitable lengths of insulated copper wire. No attempts were made to screen out external electromagnetic fields apart from shielding of the cell from direct sunlight (photopotential effects can cause significant errors in this type of measurement). The following examples are provided

Copper

Copper in aerated sea water forms a film of $Cu_2O$; the corrosion rate is initially high but decreases rapidly with immersion time. After approx. 30 min of immersion the oxide film became visible on parts of the electrodes and eventually covered both of the electrodes by the end of the test.

FIG. 9 shows noise amplitude spectra obtained after 2, 38 and 113 h of immersion. After 2 h of immersion the oxide film was still growing, the overall noise level was relatively high. The amplitude spectrum shows a clear "roll-off" at frequencies above 20 mHz, the rate of this roll-off approaches −40 dB/decade. After 38 h the noise output showed an overall drop in amplitude. Output at 1 mHz was some 20 dB lower (a factor of 10), the higher frequency output was 6 dB less than previously (a factor of 2). The slope of the roll-off remained constant, approaching −40 dB/decade. The spectrum obtained after 113 h shows similar features but the roll-off begins nearly a decade of frequency lower, indicating a possible increase of the time constant of the electrode process impedance. The noise levels are 40 dB lower at 1 mHz (a factor of 100) compared to those observed initially. At frequencies above 20 mHz the electrode noise begins to be masked by the noise background of the measurement apparatus.

Throughout this and the other tests careful investigations were made of the convection effects of aeration on the electrode noise output. By a judicious positioning of the sintered glass aerator it was possible to eliminate such effects in nearly all situations with the possible exception of the copper electrodes after prolonged periods of immersion. In that instance the electrochemical noise output was so low that effects of solution movement, building vibration, light intensity variations, etc became significant.

Aluminium

The alloy tested had a reasonable corrosion resistance to sea water and the corrosion attack had the form of a localized "etch" of the electrode surface, detailed examination revealed this to consist of a large number of small pits close together.

The noise output was found to be invariant with time and only one amplitude spectrum is shown in FIG. 10. This was recorded after 15 h of immersion. The noise output covers a wide frequency range and the sharp high frequency roll-off observed with copper electrodes is absent. The only roll-off present approaches −10 dB/decade.

Previous work indicated that the potential fluctuations associated with pit initiation are characterised by a series of sharp decreases of the electrode potential followed by exponential recoveries. It has been observed that in general such behaviour will result in a typical noise spectrum, giving a −10 dB/decade slope of the amplitude plot. Tests carried out on systems undergoing pitting corrosion lead one to conclude that this type of noise output with its shallow slope is a characteristic indication of pitting attack.

Mild Steel

After immersion the mild steel electrodes rapidly formed a film of "green rust"—presumably $Fe^{2+}$ compounds which later changed in parts to "red rust"—$Fe^{3+}$ compounds.

FIG. 11 shows noise amplitude spectra obtained after 2 and 72 h of immersion. The noise amplitude at 1 mHz was initially similar to those observed on copper and aluminium shortly after immersion but the high frequency roll-off was much sharper; approaching −50 dB/decade. With time the low frequency output decreased but the slope remained unchanged. The high frequency output seen on the 72 h spectrum is again masked by the noise floor of the measurement apparatus.

It is interesting to consider the effect of this type of behaviour of the electrode noise on any impedance measurements. The sharp increase of electrode noise with decreasing frequency should lead to a sudden increase in the scatter of the impedance data as the frequency of measurement is swept downwards, this has indeed been observed experimentally.

Crevice corrosion

None of the electrodes tested in the aforedescribed spectral analysis procedure exhibited any signs of crevice attack. However a number of other systems were tested and found that crevice corrosion gives rise to a single sharp peak 46 on the noise amplitude spectrum. This correlates well with earlier findings which show that crevice corrosion results in well defined cyclic fluctuations of the electrode potential. FIG. 12 shows the noise output typical of the early stages of crevice attack. A particular combination tested was a "memory" alloy (Ti-Ni) in 0.3M HCl solution and the frequency range covered was slightly different from that of the previous examples. The single peak at 5 mHz is just visible above the noise background present.

There is a correlation between the nature of the corrosion attack and the low frequency fluctuations of the electrode potential. The electrochemical noise output is of a constant amplitude over a range of very low frequencies and decreases in amplitude at frequencies above this range. The slope of the high frequency roll-off bears a relation to the nature of the corrosion attack. A roll-off slope of $-10$ dB/decade or less is indicative of pitting corrosion. A sharp peak at a single frequency indicates crevice attack.

The aforesaid methods provide means of monitoring corrosion of metal and the observed corrosion potential used to determine the rate of corrosion, extent of corrosion and type of corrosion. If the corroding metal part is one which must have a certain minimum structural strength the monitoring methods enable an assessment to be made of whether or not the part can still be relied on with safety and for how long it will continue to have useful life.

An alternative method of monitoring corrosion will now be described with reference to FIGS. 13 to 15 in which an essentially analogue technique is employed using the apparatus 50 in FIG. 13 rather than the essentially digital procedure using the apparatus of FIG. 2.

The apparatus 50 has leads 14, 16 for connection to first and second electrodes of any of the systems described with reference to FIGS. 1 to 8. Though apparatus similar to that in FIG. 13 can be constructed to observe the voltage amplitude fluctuation of a substantially a single frequency with the noise voltage spectrum, the apparatus 50 is arranged to observe and operate on a relatively narrow band of frequencies within the noise spectrum. To attain this the unwanted frequencies are extracted by electronic filter 52 and the output band of passed frequencies applied to a root mean square (r.m.s.) to d.c. converter 54 which observes the amplitude voltage of the frequency band and produces an output signal which is the analogue of a value of a function of the r.m.s. of the amplitude voltage of the band which value may be displayed in numerical form on a meter 56.

In a particular version of apparatus 50 the filter 52 employes three filter stages 58, 60 and 62.

The first filter stage 58 is a second order bandpass filter, centre frequency 50 mHz, Q=5, bandwidth 10 mHz and gain of 50. The second stage 60 is a slightly underdamped second order low pass stage (approximately a 1 dB dip Chebyshev response), cut off frequency of ca 0.5 Hz damping factor of 1, gain of 2. The third filter stage 62 is a first order low pass filter, cut off frequency of ca 1.6 Hz gain of 10. The stages 60, 62 are included mainly to improve the rejection of 50 Hz interference. The overall gain of the filter 52 is 1000.

The filtered and amplified signal is fed to the rms to dc converter 54 which gives an output proportional to the logarithm of the rms value of the amplitude voltage of the band pass frequency signal.

Since the noise signal is bandpass filtered i.e. dc and high frequency components are removed the rms output is mathematically equivalent to the standard deviation as determined by the digital method. The converter 54 effectively averages the rms value over a period of time set by the value of an internal capacitor, in this the averaging time constant and hence the averaging time period can be about 350 seconds. Accordingly the meter 56 can display the logarithm of the aforesaid r.m.s.

Also the logarithm of the r.m.s. can be plotted by a chart recorder 64.

In one laboratory example a pair of mild steel electrodes undergoing pitting corrosion in a 1000 ppm solution of sodium chloride were connected by leads 14, 16 to the apparatus 50 and a fragment of chart record produced by recorder 64 is shown in FIG. 14 in which the r.m.s. value is represented by the ordinate axis 66 and the spacing between each pair of lines 68 represents a time duration of fifteen minutes. The trace in FIG. 14 is rather ragged fluctuation between 100 $\mu$V and 1 mV and exhibiting random sharp peaks, for example peaks 70 and 72, followed by exponential decays. Therefore in practice if an installation has a part forming a first electrode of the same material as the laboratory electrodes and the apparatus 50 connected to that installation or apparatus 2 causes the recorder 64 to produce a chart of like character to that in FIG. 14, it can be deduced that that first electrode is undergoing pitting corrosion.

In FIG. 15 the chart record is in respect of two mild steel electrodes undergoing crevice attack in a solution of 1000 ppm sodium chloride. In FIG. 15 the trace is typical of crevice attack. It exhibits characteristic regularity in the variation of the noise output level. The spacing and size of the peaks (glitches) can be empirically related to the crevice size and the corrosion rate within the crevice. Fast peaks correspond to rapidly propagating crevice attack. Accordingly crevice attack can be deduced to be taking place on the first electrode in an installation or apparatus 2 if the resultant chart record exhibits the character of that in FIG. 15, when the apparatus 50 is used.

Also since rate of corrosion $\gamma$ is equal to r.m.s. R $\times$ C1 where C1 is a constant calculated previously, a calculation to linearise the logarithm r.m.s. value can be performed on the output from converter 54 to produce R at any instant and a further calculation preformed to produce the corrosion rate. This may be done by an arithmetic unit in meter 56 which may then display the actual corrosion rate. The output from converter 54 can also be applied to computer means 22 in FIG. 13 which can give an output on line 28 to initiate release of corrosion inhibitor if the rate exceeds a predetermined value.

If desired instead of calculating r.m.s. the converter can be an averaging device in which the signal it receives is rectified and then averaged to provide an output which is a function of the average of the amplitude voltage of band of passed frequencies. This average signal is then used in the calculation of corrosion rate in providing data representative of differing types of corrosion.

What is claimed is:

1. A method of monitoring the corrosion of a metal part wherein the part constitutes a first electrode in contact with an electrolyte, comprising; connecting a high input impedance volt meter between the first electrode and a second electrode which is in contact with the electrolyte but otherwise electrically insulated from the first electrode, the second electrode corroding in the electrolyte at a rate which does not exceed the rate of corrosion of the first electrode, said electrodes and electrolyte forming a system in which no current or voltage is applied from any source external to that system, filtering the output of the volt meter to remove (1) DC components and (2) AC components of the measured voltage having a frequency greater than a predetermined threshold frequency, and monitoring the amplitude of the filtered measured voltage, to provide an indication of the rate of corrosion of the first electrode.

2. A method as claimed in claim 1, further including determining the standard deviation of the filtered measured voltage, to provide a measure of the rate of corrosion.

3. A method as claimed in claim 1, further including determining the root mean square of the filtered measured voltage, to provide a measure of the rate of corrosion.

4. A method as claimed in claim 1, further including determining an average of the filtered measured voltage amplitude, to provide a measure of the rate of corrosion.

5. A method as claimed in claim 1, further including monitoring the filtered measured voltage in a range of frequencies below the said threshold frequency and detecting any increase in amplitude with an increase in frequency, to provide an indication of crevice corrosion.

6. A method as claimed in claim 1, further including monitoring the amplitude of the filtered measured voltage for a predetermined period and detecting any sharp peaks in the relationship between the monitored voltage and time, to provide an indication of pitting corrosion.

7. An apparatus for monitoring the corrosion of a metal part, wherein the part constitutes a first electrode in contact with an electrolyte, comprising a second electrode in contact with said electrolyte but otherwise electrically insulated from said first electrode, a high input impedance volt meter connected to said first electrode and said second electrode, means for filtering the output of the volt meter to remove (1) DC components and (2) AC components of the measured voltage having a frequency greater than a predetermined threshold frequency, and means for monitoring the output of the filtering means to provide an indication of the rate of corrosion of the first electrode.

8. An apparatus according to claim 7, comprising means responsive to the monitoring means for introducing a corrosion inhibitor into the electrolyte.

9. An apparatus according to claim 7, comprising means responsive to the monitoring means for introducing gas bubbles into the electrolyte.

* * * * *